United States Patent [19]
Merritt et al.

[11] Patent Number: 6,071,900
[45] Date of Patent: Jun. 6, 2000

[54] HETEROCYCLIC COMPOUNDS AND THEIR USE

[75] Inventors: Leander Merritt; John S. Ward, both of Indianapolis, Ind.

[73] Assignee: Eli Lilly and Company, Indianapolis, Ind.

[21] Appl. No.: 09/274,145

[22] Filed: Mar. 22, 1999

Related U.S. Application Data

[62] Division of application No. 08/844,307, Apr. 10, 1997, which is a division of application No. 08/443,674, Jun. 1, 1995, Pat. No. 5,998,404, which is a continuation-in-part of application No. 08/327,741, Oct. 24, 1994, Pat. No. 5,605,908.

[51] Int. Cl.$^7$ ...................... A61K 31/495; C07D 401/12; C07D 451/02; C07D 403/12
[52] U.S. Cl. .................... 514/216; 514/253; 544/405; 544/408
[58] Field of Search .................................... 544/405, 408; 514/253, 216; 540/593

[56] References Cited

U.S. PATENT DOCUMENTS

| | | | |
|---|---|---|---|
| 4,837,241 | 6/1989 | Jensen et al. | 514/340 |
| 4,894,453 | 1/1990 | Yaso et al. | 544/354 |
| 5,041,455 | 8/1991 | Sauerberg et al. | 514/342 |
| 5,082,843 | 1/1992 | Cliffe et al. | 514/253 |
| 5,286,864 | 2/1994 | Walther et al. | 546/137 |
| 5,328,923 | 7/1994 | Sauerberg et al. | 514/340 |
| 5,328,924 | 7/1994 | Sauerberg et al. | 514/340 |
| 5,414,009 | 5/1995 | Olesen et al. | 514/299 |
| 5,418,240 | 5/1995 | Sauerberg et al. | 514/305 |
| 5,508,405 | 4/1996 | Walther et al. | 546/133 |
| 5,512,574 | 4/1996 | Husbands et al. | 514/253 |
| 5,665,745 | 9/1997 | Alt et al. | 514/362 |
| 5,731,323 | 3/1998 | Whittamore | 514/305 |

FOREIGN PATENT DOCUMENTS

| | | |
|---|---|---|
| 2042860 | 11/1991 | Canada . |
| 491 374 A1 | 6/1992 | European Pat. Off. . |
| 94/08992 | 4/1984 | WIPO . |
| WO 94/14805 WO | 7/1994 | WIPO . |
| 95/05174-A1 WO | 2/1995 | WIPO . |
| 95/05379-A1 | 2/1995 | WIPO . |

OTHER PUBLICATIONS

Ward et al, *J. Med. Chem.* 35 pp. 4011–4019, 1992.
Quirion et al, *TIPS* pp. 80–84, 1989.
Derwent Abstract 43103T–BDE (Feb. 21, 1969).
Derwent Abstract 23326A/13 (May 10, 1976).
Derwent Abstract 21307 D/12 (Apr. 7, 1980).
Derwent Abstract 61811V/35 (Feb. 20, 1973).
Derwent Abstract 18366B/10 (Jul. 27, 1977).
Derwent Abstract 10251B/06 (Jul. 8, 1977).
Derwent Abstract 83–778153/40 Jul. 16, 1982).
Derwent Abstract 83–7653115/38 (Aug. 1, 1981).
Derwent Abstract 85–112228/19 (Oct. 1931).
Derwent Abstract 88–008621/02 (Jun. 30, 1986).
Derwent Abstract 88–256990/36 (Feb. 27, 1987).
Mathew, et al., Am. J. Psychiatry, 137:9, 1118–1120 (1980).
Sim, M. and Houghton, H., J. of Nervous and Mental Disease, 143:6, 484–491 (1966).
Rapaport, et al., Biol. Psychiatry, 29, 658–664 (1991).
Chemical Abstracts, 117:13, p. 766 (Sep. 28, 1992), No. 131387.
Chemical Abstracts, 117:3, p. 702 (Jul. 20, 1992), N. 26428.
Chemical Abstracts, 109:21, p. 712 (Nov. 21, 1988), No. 190381.
Chemical Abstracts, 106:3, p. 601 (Jan. 9, 1987), No. 18488.
Chemical Abstracts, 84:19, p. 482 (May 10, 1976), No. 135479.
Newhouse, et al., Drug Development Research, 38, pp. 278–289 (1996).
Aubert, et al., J. of Neurochemistry, "Comparative Alterations of Nicotinic and Muscarinic Binding Sites in Alzheimer's and Parkinsons's Diseases," pp. 529–541 (1992).
Datzung, B. G., Basic & Clinical Pharmacology, (Appleton & Lange, Norwald), pp. 92–94 (1995).

*Primary Examiner*—Emily Bernhardt
*Attorney, Agent, or Firm*—David M. Stemerick; MaCharri R. Vorndran Jones

[57] ABSTRACT

The present invention relates to therapeutically active azacyclic or azabicyclic compounds, a method of preparing the same and to pharmaceutical compositions comprising the compounds. The novel compounds are useful in treating diseases in the central nervous system caused by malfunctioning of the muscarinic cholinergic system.

13 Claims, No Drawings

HETEROCYCLIC COMPOUNDS AND THEIR USE

This application is a division of application Ser. No. 08/844,307, filed Apr. 10, 1997, which is a division of application Ser. No. 08/443,674, filed Jun. 1, 1995 now U.S. Pat. No. 5,998,404, which is a continuation-in-part of application Ser. No. 08/327,741, filed Oct. 24, 1994, now U.S. Pat. No. 5,605,908.

FIELD OF THE INVENTION

The present invention relates to therapeutically active azacyclic or azabicyclic compounds, a method of preparing the same and to compositions for pharmaceutical or veterinary use comprising the compounds and a carrier therefore. The novel compounds are useful as stimulants of the cognitive function of the forebrain and hippocampus of mammals and especially in the treatment of Alzheimer's disease.

BACKGROUND OF THE INVENTION

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic receptors in the forebrain and hippocampus still exist. Therefore, cholinergic agonists are useful in the treatment of Alzheimer's disease, in halting its progression, and in improving the cognitive functions of elderly people.

The compounds of this invention are also useful analgesic agents and therfore useful in the treatment of severe painful conditions.

Furthermore, the compounds of this invention are useful in the treatment of glaucoma, psychosis, mania, bipolar disorder, schizophrenia or schizophreniform conditions, depression; sleeping disorders, epilepsy, and gastrointestinal motility disorders.

SUMMARY OF THE INVENTION

It is an object of the invention to provide new muscarinic cholinergic compounds and nicotinic cholinergic compounds.

The novel compounds of the invention are heterocyclic compounds having the Formula I or I'

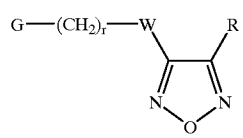

I

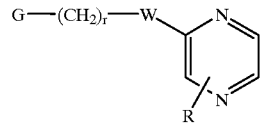

I' wherein
W is oxygen or sulphur;
R is hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $-CF_3$, $-CN$, Y, phenyl or phenoxy wherein phenyl or phenoxy is optionally substituted with halogen, $-CN$, $C_{1-4}$-alkyl, $C_{1-4}$-alkoxy, $-OCF_3$, $-CF_3$, $-CONH_2$ or $-CSNH_2$; or
R is phenyl or benzyloxycarbonyl, each of which is optionally substituted with halogen, $-CN$, $C_{1-4}$-alkyl, $C_{1-4}$-alkoxy, $-OCF_3$, $-CF_3$, $-CONH_2$ or $-CSNH_2$; or
R is $-OR^5Y$, $-SR^5Y$, $OR^5-Z-Y$, $-SR^5ZY$, $-O-R^5-Z-R^4$ or $-S-R^5-Z-R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and
G is selected from one of the following azacyclic or azabicyclic ring systems:

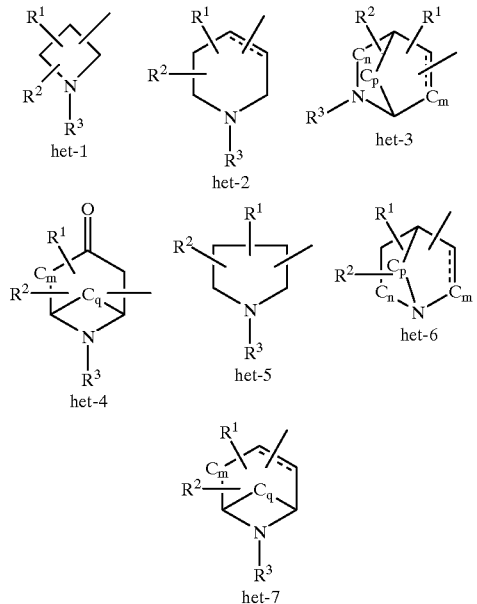

or G can optionally be substituted $C_3-C_8$ cycloalkyl or optionally substituted $C_{1-6}$-alkyl wherein the substitution is $-NR^6R^7$;
$R^6$ and $R^7$ independently are hydrogen, $C_{1-6}$-alkyl; or $R^6$ and $R^7$ together with the nitrogen atom optionally form a 4- to 6-member ring;
$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with $-OH$, $-COR^{6'}$, $CH_2$-OH, halogen, $-NH_2$, carboxy, or phenyl;

$R^3$ is hydrogen, $C_{1-5}$-alkyl, $C_{2-5}$-alkenyl or $C_{2-5}$-alkynyl;

$R^6$ is hydrogen, $C_{1-6}$-alkyl;

n is 0, 1 or 2;

m is 0, 1 or 2;

p is 0, 1 or 2;

q is 1 or 2;

r is 0, 1 or 2;

... is a single or double bond; or a pharmaceutically acceptable salt or solvate thereof.

It is to be understood that the invention extends to each of the stereoisomeric forms of the compounds of the present invention as well as the pure diastereomeric, pure enatiomeric, and racemic forms of the compounds of Formula I and I'.

DETAILED DESCRIPTION

As used herein the term "treating" includes prophylaxis of a physical and/or mental condition or amelioration or elimination of the developed physical and/or mental condition once it has been established or alleviation of the characteristic symptoms of such condition.

As used herein with reference to the G substituent, the —$(CH_2)_r$-W-oxadiazole or —$(CH_2)_r$-W-pyrazine moiety can be attached at any carbon atom of the azacyclic or azabicyclic ring. Further, $R^1$ and $R^2$ of the G substituent may be present at any position, including the point of attachment of the —$(CH_2)_r$-W-oxadiazole or —$(CH_2)_r$-W-pyrazine moiety.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

As used herein with reference to the G substituent, the numbering shall be as follows:

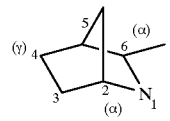

het-5

As used herein the term α shall refer to a position on the G substituent which is one position away from the N atom of the G substituent. For example, in the following illustration (1E), both positions 2 and 6 are considered α. The term λ shall refer to the position on the G substituent which is opposite the N atom. For example, in the illustration (1E), position 4 is considered λ. Likewise, β shall refer to the 3 and 5 position in the illustration.

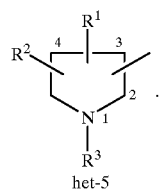

As used herein with reference to the G substituent, the phrase "$R^6$ and $R^7$ together with the nitrogen atom optionally form a 4- to 6-member ring" means that $R^6$ and $R^7$ are each independently hydrogen, $C_1$–$C_6$ alkyl; the $R^6$ and $R^7$ groups may optionally join to form a 4- to 6-member ring including the nitrogen. For example, optionally joined groups include, but not limited to:

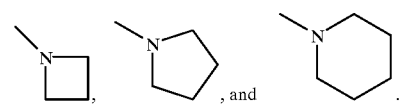

As used herein the phrase "interacting with a muscarinic cholinergic receptor" shall include compounds which block muscarinic cholinergic receptors or modulate such receptors. Likewise, the term "interacting with a nicotinic cholinergic receptor" shall include compounds which block or modulate the receptor. The phrase shall include the effect observed when compounds act as agonists, partial agonists and/or antagonists at a cholinergic receptor.

As used herein, the term "alkoxide metal" means a metal suitable for alkoxide formation. Such alkoxide metals include, but are not limited to, $Li^+$, $K^+$, $Na^+$, $Cs^+$, and $Ca^{++}$. Especially preferred alkoxide metals include $Li^+$, $K^+$, and $Na^+$.

As used herein, the term "halogen" means Cl, Br, F, and I. Especially preferred halogens include Cl, Br, and I.

The terms "$C_1$–$C_{n'}$ alkyl" wherein n' can be from 2 through 15, as used herein, represent a branched or linear alkyl group having from one to the specified number of carbon atoms. Typical $C_1$–$C_6$ alkyl groups include methyl, ethyl, n-propyl, iso-propyl, butyl, iso-butyl, sec-butyl, tert-butyl, pentyl, hexyl and the like.

The terms "$C_2$–$C_{n'}$ alkenyl" wherein n' can be from 3 through 10, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=CHCH$_2$CH$_3$), hexenyl, pentenyl, and the like.

The term "$C_2$–$C_5$ alkynyl" refers to an unsaturated branched or linear group having from 2 to 5 carbon atoms and at least one triple bond. Examples of such groups include, but are not limited to, 1-propynyl, 2-propynyl, 1-butynyl, 2-butynyl, 1-pentynyl, and the like.

The terms "halogen($C_1$–$C_6$)alkyl" and "halogen($C_2$–$C_6$) alkenyl" refer to alkyl or alkenyl substituents having one or more independently selected halogen atoms attached at one or more available carbon atoms. These terms include, but are not limited to, chloromethyl, 1-bromoethyl, 2-bromoethyl, 1,1,1-trifluoroethyl, 1,1,2-trifluoroethyl, 1,2,2-trifluoroethyl, 2,2,2-trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, 1-chloroethylenyl, 2-chloroethylenyl, 5-fluoro-3-pentenyl, 3-chloro-2-bromo-5-hexenyl, 3-chloro-2-bromobutyl, trichloromethyl, 1,1-dichloroethyl, 1,2-dichloroethyl, 2,2-dichloroethyl, 1,4-dichlorobutyl, 3-bromopentyl, 1,3-dichlorobutyl, 1,1-dichloropropyl, and the like.

The term "$C_2$–$C_{10}$ alkanoyl" represents a group of the formula C(O) ($C_1$–$C_9$) alkyl. Typical $C_2$–$C_{10}$ alkanoyl groups include acetyl, propanoyl, butanoyl, and the like.

The term "($C_1$–$C_6$ alkyl) amino" refers to a monoalkylamino group. Examples of such groups are methylamino, ethylamino, iso-propylamino, n-propylamino, (n-propyl) amino, (iso-propyl)amino, n-propylamino, t-butylamino, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "substituted($C_5$–$C_n$) cycloalkyl" refers to a cycloalkyl group as described supra wherein the cycloalkyl group may be substituted with from one to four substituents independently selected from the group consisting of hydrogen, $C_1$–$C_6$ alkyl, $NO_2$, halogen, halogen($C_1$–$C_6$) alkyl, halogen($C_2$–$C_6$)alkenyl, $C_2$–$C_6$ alkenyl, $CO_2R^{20}$, ($C_1$–$C_6$ alkyl) amino, —$SR^{20}$, and $OR^{20}$; wherein $R^{20}$ is selected from the group consisting of $C_{1-15}$-alkyl, $C_{2-15}$-alkenyl, and $C_{2-15}$-alkynyl.

The term "$C_3$–$C_8$ cycloalkyl-($C_1$–$C_3$)alkyl" represents an alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl", represents an olefinically unsaturated ring having five to eight carbon atoms. Such groups include, but are not limited to, cyclohexyl-1,3-dienyl, cyclohexenyl, cyclopentenyl, cycloheptenyl, cyclooctenyl, cyclohexyl-1,4-dienyl, cycloheptyl-1,4-dienyl, cyclooctyl-1,3,5-trienyl and the like.

The term "substituted ($C_5$–$C_8$) cycloalkenyl" refers to a cycloalkenyl group as described supra wherein the cycloalkenyl group may be substituted with from one to four substituents independently selected from the group consisting of hydrogen, $C_1$–$C_6$ alkyl, $NO_2$, halogen, halogen ($C_1$–$C_6$)alkyl, halogen($C_2$–$C_6$)alkenyl, $C_2$–$C_6$ alkenyl, $COR^{20}$, $C_2$–$C_{10}$ alkanoyl, $C_7$–$C_{16}$ arylalkyl, $CO_2R^{20}$, ($C_1$–$C_6$ alkyl) amino, —$SR^{20}$, and —$OR^{20}$. Wherein $R^{20}$ is selected from the group consisting of $C_{1-15}$-alkyl, $C_{2-15}$-alkenyl, $C_{2-15}$-alkynyl.

The term "$C_5$–$C_8$ cycloalkenyl-($C_1$–$C_3$)alkyl" represents a $C_1$–$C_3$ alkyl group substituted at a terminal carbon with a $C_5$–$C_8$ cycloalkenyl group.

As used herein, the phrase "5 or 6 membered heterocyclic group" means a group containing from one to four N, O or S atom(s) or a combination thereof, which heterocyclic group is optionally substituted at carbon or nitrogen atom(s) with $C_{1-6}$-alkyl, —$CF_3$, phenyl, benzyl or thienyl, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having 3-heteroatoms; 6-membered heterocycles with one heteroatom (e.g. pyridine, quinoline, isoquinoline, phenanthrine, 5,6-cycloheptenopyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-member heterocycles with four heteroatoms. Particularly preferred are thiophenes, pyridines, and furans.

The term "heteroaryl" refers to a group which is a 5 or 6 membered heterocycle containing one to four N, O, or S atoms or a combination thereof.

As used herein the term "carboxy" refers to a substituent having the common meaning understood by the skilled artisan, wherein the point of attachment may be through the carbon or oxygen atom of the group.

As used herein the term "aryl" means an organic radical derived from an aromatic hydrocarbon by the removal of one atom; e.g., phenyl or naphthyl, most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The term "aryl($C_1$–$C_3$) alkyl refers to any aryl group which is attached to the parent moiety via the alkyl group.

As used herein the term malfunctioning of the muscarinic cholinergic system" shall have the meaning accepted by the skilled artisan. Likewise, the term "malfunctioning of the nicotinic cholinergic system" shall have the art recognized meaning. For example the term shall refer to, but is not in any way limited to, conditions such as glaucoma, psychosis, schizophrenia or schizophreniform conditions, depression, sleeping disorders, epilepsy, and gastrointestinal motility disorders. Other such conditions include Alzheimer's Disease and incontinence.

Compounds of this invention can be prepared by a) reacting a compound of formula II

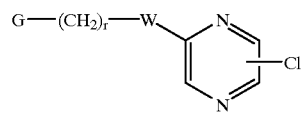

II wherein G, W and r have the meaning defined above with h$^+$QR wherein h$^+$ is an alkoxide metal; Q is O or S and R has the meaning defined above, or b) reacting a compound of formula III or IV

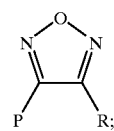

III

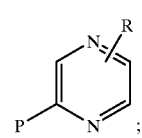

IV wherein P is $R^9SO_2$ or halogen; $R^9$ is $C_{1-8}$ straight or branched chain alkyl or aryl; and R has the meaning defined above; with G—(CH$_2$)$_r$—W$^-$—h$^+$ wherein h$^+$, G, W and r have the meanings defined above.

The compounds of this invention can be prepared as described supra, and by using the chemical processes illustrated in Scheme I. The starting materials for the illustrated process are commercially available or may be prepared using methods known to the skilled artisan.

Scheme I

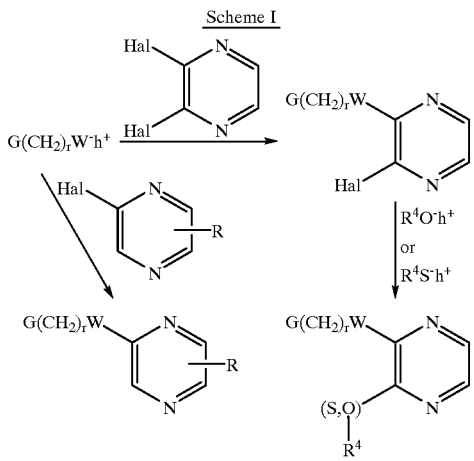

As used in Scheme I, R, h+, and G are as defined supra. As used in Scheme I, the term "Hal" refers to Cl, Br, I, and R⁹SO₂.

Compounds of this invention may be prepared by the process illustrated in Scheme II Scheme II

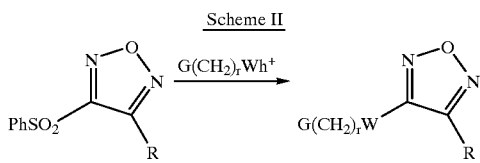

The artisan will recognize that the starting materials for the process of Scheme II are commercially available or can be prepared using methods familiar to the skilled artisan.

Compounds of Formula I wherein R is an R⁴ group, can be prepared using methods well known in the art. See for example, U.S. Pat. No. 5,043,345.

Further, compounds of Formula I may be prepared using the process illustrated in the following Scheme III Scheme III

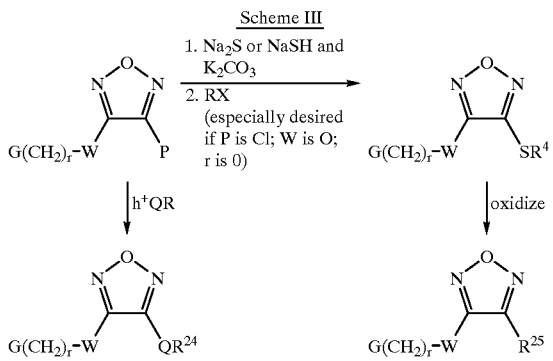

As used in Scheme III, Q may be N, O or S; $R^{24}$ is selected from the group consisting of hydrogen, $R^4$, $R^5$, $R^6$, and $R^7$; $R^{25}$ is selected from the group consisting of $SOR^4$ and $SO_2R^4$; all other meanings are as defined supra.

Additional compounds of Formula I may be prepared using the process illustrated by Scheme IV.

Scheme IV

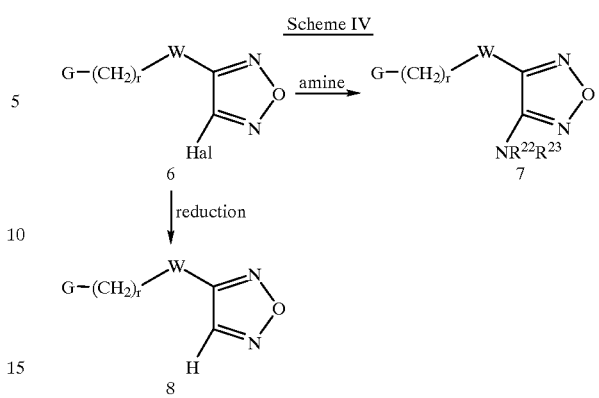

As used in Scheme IV, Hal, W, r, and G are as defined supra. As used in Scheme IV, $R^{22}$ and $R^{23}$ are independently selected from the group consisting of hydrogen, $R^6$ and $R^7$.

When the G substituent contains a secondary nitrogen protected by a protecting group, the protecting group may be removed using standard methods known to the skilled artisan. An especially preferred protecting group is carbamate. One particularly useful reference concerning protecting groups is Greene, *Protecting Groups in Organic Synthesis*, (John Wiley & Sons, New York, 1981).

Certain compounds of this invention may more preferredly be prepared using the process of Scheme V.

Scheme V

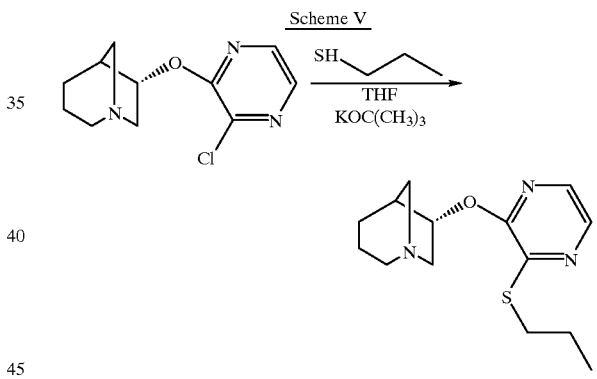

Potassium t-butoxide or another appropriate alkali metal base was added at about 0° C. to an alkylthiol in THF and stirred. The haloopyrazine was added and the reaction stirred at about room temperature. A sample of about 1 N acid was added and the aqueous solution washed. The pH was adjusted to about 12.0. The product was extracted, dried and evaporated. The salt was optionally formed using standard methods.

Certain of the compounds of this invention can more preferredly be prepared using the process illustrated by Scheme VI.

Scheme VI

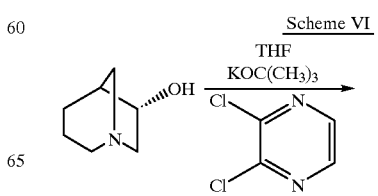

-continued

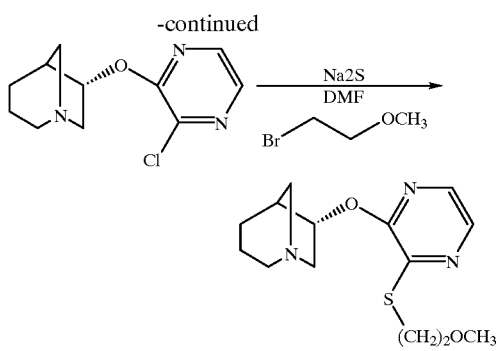

The alcohol was added to a mixture of potassium t-butoxide in THF at about room temperature. The reaction was cooled to about 5° C. The 2,3-dichloropyrazine in THF was added to the mixture. The reaction mixture was stirred at about room temperature for about 2 hrs, condensed, diluted with water and ethyl acetate. The organic solution was dried and condensed. The chloropyrazine derivative and sodium sulfide ($Na_2S \cdot 9H_2O$), were heated in DMF at about 50° C. for about 3.5 hr, cooled to about 0° C. Then 2-Bromoethylmethylether was added. The reaction was stirred at about room temperature overnight and diluted with ethyl acetate and about 5 N acid. The aqueous layer was washed and the pH adjusted to about 12.0. The product was extracted, dried, condensed and purified by HPLC. The salt form of the product was optionally formed using standard methods.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labeled by $^3$H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 mL 20 nM Hepes pH: 7.4, with an Ultra-Turrax homogenizer. The homogenizer is rinsed with 10 mL of buffer and the combined suspension centrifuged for 15 min. at 40,000×g. The pellet is washed three times with buffer. In each step the pellet is homogenized as before in 2×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 25 μL of test solution and 25 μL of $^3$H-Oxotremorine (1.0 nM, final concentration) mixed and incubated for 30 min. at 25° C. Non-specific binding is determined in triplicate using arecoline (1 μg/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of $IC_{50}$. The test value will be given as $IC_{50}$ (the concentration (nM) of the test substance which inhibits the specific binding of $^3$H-oxo by 50%).

$IC_{50}$=(applied test substance concentration) $x(C_x/C_o-C_x)$ nM where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$HPRZ (pirenzepine, [N-methyl-$^3$H]) binding to rat cerebral cortex membranes.

Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2×10 mL of buffer and the combined suspension centrifuged for 15 min. at 40,000×g. The pellet is washed three times with buffer. in each step the pellet is homogenized as before in 3×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 20 μL of test solution and 25 μL of $^3$HPRZ (1.0 nM, final conc.), mixed and incubated for 60 min. at 20° C. Non-specific binding is determined in triplicate using atropine (1.0 μg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of $IC_{50}$.

The test value will be given as $IC_{50}$ (the concentration (nM) of the test substance which inhibits the specific binding of $^3$HPRZ by 50%). $IC_{50}$=(applied test substance concentration) $x(C_x/C_o-C_x)$nM where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound | $^3$H-Oxo-M $IC_{50}$, nM | $^3$HPRZ $IC_{50}$, nM |
| --- | --- | --- |
| 1 | 81 | 56 |
| 2 | 374 | 253 |
| 3 | 19.3 | 14.5 |
| 6 | 2.5 | 0.9 |
| 4 | 25 | 21 |
| 5 | 40 | 32 |
| 7 | 16 | 6.7 |
| 8 | 1040 | >1000 |

TABLE 1-continued

| Compound No. | Oxo-M IC-50, nM | Pir IC-50, nM |
|---|---|---|
| 9 | 36 | 30 |
| 10 | 354 | 223 |
| 11 | 56 | 53 |
| 12 | 25 | 13 |
| 13 | 74 | 42 |
| 14 | 26 | 21 |
| 15 | 14 | 13 |
| 16 | 39 | 23 |
| 17 | 17 | 4.5 |
| 18 | 21 | 5.4 |
| 19 | 121 | 108 |
| 20 | 245 | 246 |
| 21 | 26 | 123 |
| 22 | 140 | 52 |
| 23 | 4.9 | 2.7 |
| 24 | 2.2 | 0.54 |
| 25 | 180 | 680 |
| 26 | >1000 | >1000 |
| 27 | >1000 | >1000 |
| 28 | >10,000 | 5710 |
| 29 | 1.7 | 0.68 |
| 30 | 4.4 | 0.82 |
| 41 | 3.2 | 1.6 |
| 42 | 9.1 | 4.8 |
| 43 | 8.1 | 2.2 |
| 31 | 3.4 | 1.7 |
| 32 | 3.9 | 4.0 |
| 33 | 1.5 | 0.7 |
| 34 | 2.0 | 0.66 |
| 35 | 3.2 | 0.54 |
| 36 | 0.34 | 5.8 |
| 37 | 1.3 | 0.76 |
| 38 | 6.2 | 3.3 |
| 39 | 10 | 80 |
| 40 | 60 | 17 |

Nicotinic Channel Receptor Binding Protocol:

The activity of the compounds claimed herein at the nicotinic receptor can be accomplished by the following assay.

Binding of [$^3$H]-cystine to nicotinic receptors was accomplished using crude synaptic membrane preparations from whole rat brain (Pabreza et al. *Molecular Pharmacol.*, 1990, 39:9). Washed membranes were stored at about −80° C. prior to use. Frozen aliquots were slowly thawed and resuspended in 20 volumes of buffer (containing: 120 nM NaCl, 5 mM KCl, 2 mM MgCl$_2$, 2 mM Tris-Cl, ph 7.4 @4° C.). After centrifuging at 20,000×g for 15 minutes, the pellets were resuspended in about 30 volumes of buffer. Homogenate (containing about 125–150 ug protein) was added to tubes containing concentrations of test compound and [$^3$H-cystine] (1.25 nM) in a final volume of 500 uL. Samples were incubated for about 60 minutes at about 4° C., then rapidly filtered through GF/B filters presoaked in 0.5% polyethylimine using 3×4 mL of ice cold buffer. The filters were counted.

Nicotinic Binding Data

| Compound No. | Cystine K$_i$, nM |
|---|---|
| 26 | 130 |
| 19 | 2730 |
| 17 | 21400 |
| 21 | 130 |
| 18 | 580 |
| 22 | 210 |
| 27 | 110 |
| 6 | 5490 |

Some examples of compounds contemplated by this invention include, but are not limited to: (±)-3-butylthio-4-(azabicyclo[2.2.2]octyl-3-oxy)-1,2,5-oxadiazole, (±)-3-(2-butyloxy)-4-[(±)-3-azabicyclo[2.2.2]octyloxy)-1,2,5-oxadiazole, (±)-3-butyloxy-4-[endo-(±)-6-[1-azabicyclo[3.2.1]octyloxy)]-1,2,5-oxadiazole, 2-[exo-(±)-3-[1-azabicyclo[3.2.1]octyloxy)]pyrazine, 3-(2,2,3,3,4,4,4-heptaflurorobutyloxy)-4-[(±)-3-(1-azabicyclo[2.2.2]octyloxy)]-1,2,5-oxadiazole, 3-methoxy-4-(1-azabicyclo[2.2.2]octyl-3-oxy)-1,2,5-oxadiazole, 3-pentylthio-4-(1-azabicyclo[2.2.2]ocytl-3-oxy)-1,2,5-oxadiazole, trans-3-butyloxy-4-(2-dimethylaminocyclopentyloxy)-1,2,5-oxadiazole, 3-butylthio-4-(3-azetidinyloxy)-1,2,5-oxadiazole, 3-(3-N-(2-thiazolidonyl)propylthio)-4-(1-azabicyclo[2.2.2]octyl-3-oxy)-1,2,5-oxadiazole, 3-chloro-4-(1-azabicyclo[3.2.1]octyl-6-oxy)-1,2,5-oxadiazole, 3-(2-2-thio-5-trifluoromethylthienyl)ethylthio)-4-azabicyclo[2.2.2]octyl-3-oxy)-1,2,5-oxadiazole, 3-butylthio-2-(1-azabicyclo[2.2.2]ocytl-3-oxy)]pyrazine, 3-butyloxy-2-[3-±-endo-(1-azabicyclo[2.2.1]heptyloxy)]pyrazine, 3-butylthio-4-[3-±-endo-(1-azabicyclo[2.2.1]heptyloxy))-1,2,5-oxadiazole, 3-(2-butynyloxy)-2-[6-±-endo-(1-azabicyclo[3.2.1]octyloxy)pyrazine, 3-hexylthio-2-[6-±-exo-(2-azabicyclo(2.2.1]heptyloxy)]pyrazine, 3-hexyloxy-4-[6-±-endo-(2-azabicyclo[2.2.2]ocyloxy)]-1,2,5-oxadiazole, 3-(3-phenylpropynylthio)-2-[2-±-exo-(7-azabicyclo[2.2.1]heptyloxy)]pyrazine, 3-(4,4,4-trifluorobutylthio)-4-[2-±-exo-(7-azabicyclo[2.2.1]heptyloxy)]-1,2,5-oxadiazole, 3-(2-phenoxyethylthio)-4-[3-±-endo-(1-azabicyclo[3.2.1]octyloxy)]-1,2,5-oxadiazole, 3-(2-methylthioethoxy)-2-[3-±-exo-(1-azabicyclo[3.2.1]octyloxy)]pyrazine, 3-propargyl-2-[4-(1-azabicyclo[2.2.1]heptyloxy)]pyrazine, 3-(5-hexenyloxy)-4-[7-±-endo-(2-azabicyclo[2.2.1]heptyloxy)]-1,2,5-oxadiazole, 3-butyl-4-[5-(1-azabicyclo[3.2.1]octyloxy)]-1,2,5-oxadiazole, 3-cyclopropylmethylthio-2-[2-±-exo-(8-azabicyclo[3.2.1]octyloxy)]pyrazine, and 3-cyclobutylmethyl-4-[2-±-endo-(8-azabicyclo[3.2.1]octyloxy)]-1,2,5-oxadiazole.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated, the body weight of the subject to be treated, and the preference and experience of the physician or prescribing caregiver in charge.

The route of administration may be any route, which effectively transports the active compound to the appropriate or desired site of action, such as oral or parenteral e.g. rectal, transdermal, depot, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

In order to more fully illustrate the operation of this invention, the following formulation examples are provided. The examples are illustrative only, and are not intended to limit the scope of the invention in any way.

FORMULATION 1

A typical tablet, appropriate for use in this method, may be prepared using conventional techniques and may contain:

|  | Amount per Tablet | Concentration by Weight (%) |
| --- | --- | --- |
| (±)-Endo-3-butylthio-2-(1-azabicyclo [3.2.1]-octyl-6-oxy)-1,2,5-oxadiazole | 5.0 mg | 4.7 |
| Lactosum | 67.8 mg Ph. Eur. | 64.2 |

-continued

|  | Amount per Tablet | Concentration by Weight (%) |
| --- | --- | --- |
| Avicel ® | 31.4 mg | 29.8 |
| Amberlite ® | 1.0 mg | 1.0 |
| magnesium stearate | 0.25 mg Ph. Eur. | 0.3 |
|  | 105.45 mg | 100 |

FORMULATION 2

Hard gelatin capsules are prepared using the following ingredients:

|  | Amount per Tablet | Concentration by Weight (%) |
| --- | --- | --- |
| (±)-Exo-3-butyloxy-2-(N-methyl-8-azabicyclo-[3.2.1 ]octyl-3-oxy)-pyrazine | 0.1 mg | 0.05 |
| starch dried | 200 mg | 95.2 |
| magnesium stearate | 10 mg | 4.8 |
|  | 210.1 mg | 100 |

The above ingredients are mixed and filled into hard gelatin capsules in 210.1 mg quantities.

FORMULATION 3

Suspensions each containing 1 mg of medicament per 5 mL dose are as follows:

|  | Amount per 5 mL of suspension |
| --- | --- |
| (±)-3-(3-phenylethylthio)-4-(1-azabicyclo [2.2.2 ]octyl-3-oxy)-1,2,5-oxadiazole | 1 mg |
| sodium carboxymethyl cellulose | 50 mg |
| syrup | 1.25 mL |
| benzoic acid solution | 0.10 mL |
| flavor | q.v. |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The compounds of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be adminstered as a feed additive or in bulk form.

The intermediates and processes of the present invention are useful for preparing compounds having beneficial muscarinic receptor activity. The compounds of the present invention have such useful muscarinic receptor activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of formula I are:

A) W is S;
B) r is 1 or 2;
C) G is selected from het-1 and het-5;
D) G is unsaturated;
E) G is het-4;
F) G is an azabicycle having 7 ring carbon atoms and a nitrogen atom;
G) G is het-6;
H) r is 0;
I) R is selected from halogen, $-OR^5Y$, $-SR^5Y$, $-OR^5ZY$, $-SR^5ZY$, $-OR^5ZR^4$, $-SR^5ZR^4$, $-OR^4$, and $-SR^4$;
J) W is O;
K) m is 1;
L) n is 1;
M) p is 2;
N) G is het-3
O) G is het-2
P) a compound of Formula I
Q) a compound of Formula I'
R) a compound of Formula I
wherein W is oxygen or sulphur;

R is selected from the group consisting of hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl); $R^4$ is selected from the group consisting of $C_{1-15}$-alkyl, $C_{2-15}$-alkenyl, and $C_{2-15}$-alkynyl, each of which is optionally substituted with one or more independently selected from the group consisting of halogen(s), $-CF_3$, $-CN$, Y, phenyl and phenoxy wherein phenyl or phenoxy is optionally substituted with one or more selected from the group consisting of halogen, $-CN$, $C_{1-4}$-alkyl, $C_{1-4}$-alkoxy, $-OCF_3$, $-CF_3$, $-CONH_2$ and $-CSNH_2$; or R is phenyl or benzyloxycarbonyl, each of which is optionally substituted with one or more substituents independently selected from the group consisting of halogen, $-CN$, $C_{1-4}$-alkyl, $C_{1-4}$-alkoxy, $-OCF_3$, $-CF_3$, $-CONH_2$ and $-CSNH_2$; or R is selected from the group consisting of $-OR^5Y$, $-SR^5Y$, $OR^5-Z-Y$, $-SR^5ZY$, $-O-R^5-Z-R^4$ and $-S-R^5-Z-R^4$;

Z is oxygen or sulphur;

$R^5$ is selected from the group consisting of $C_{1-15}$-alkyl, $C_{2-15}$-alkenyl, and $C_{2-15}$-alkynyl;

Y is a 5 or 6 membered heterocyclic group; and

G is selected from one of the following azacyclic or azabicyclic ring systems:

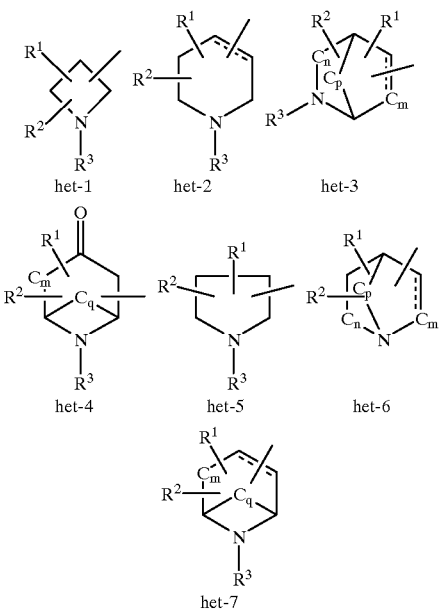

or

G can optionally be substituted $C_3$–$C_8$ cycloalkyl wherein the substitution is $-NR^6R^7$;

$R^6$ and $R^7$ independently are selected from the group consisting of hydrogen and $C_{1-6}$-alkyl; or $R^6$ and $R^7$ together with the nitrogen atom optionally form a 4- to 6-member ring;

$R^1$ and $R^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with a subsituent independently selected from the group consisting of $-OH$, $-COR^{6'}$, $CH_2-OH$, halogen, $-NH_2$, carboxy, and phenyl;

$R^3$ is selected from the group consisting of hydrogen, $C_{1-5}$-alkyl, $C_{2-5}$-alkenyl and $C_{2-5}$-alkynyl;

$R^{6'}$ is selected from the group consisting of hydrogen and $C_{1-6}$-alkyl;

n is 0, 1 or 2;
m is 0, 1 or 2;
p is 0, 1 or 2;
q is 1 or 2;
r is 0, 1 or 2;
. . . is a single or double bond;

provided that when W is O and G is a saturated azabicyclic group having from 7 to 11 ring carbon atoms and a nitrogen atom wherein the nitrogen atom is separated from the W atom by 2 to 3 ring carbon atoms;

or a pharmaceutically acceptable salt or solvate thereof;

S) a compound of Formula I'
wherein

W is oxygen or sulphur;

R is selected from the group consisting of hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl); $R^4$ is selected from the group consisting of $C_{1-15}$-alkyl, $C_{2-15}$-alkenyl, and $C_{2-15}$-alkynyl, each of which is optionally substituted with one or more independently selected from the group consisting of halogen(s), —$CF_3$, —CN, Y, phenyl and phenoxy wherein phenyl or phenoxy is optionally substituted with one or more selected from the group consisting of halogen, —CN, $C_{1-4}$-alkyl, $C_{1-4}$-alkoxy, —$OCF_3$, —$CF_3$, —$CONH_2$ and —$CSNH_2$; or R is phenyl or benzyloxycarbonyl, each of which is optionally substituted with one or more substituents independently selected from the group consisting of halogen, —CN, $C_{1-4}$-alkyl, $C_{1-4}$-alkoxy, —$OCF_3$, —$CF_3$, —$CONH_2$ and —$CSNH_2$; or R is selected from the group consisting of —$OR^5Y$, —$SR^5Y$, $OR^5$—Z—Y, —$SR^5ZY$, —O—$R^5$—Z—$R^4$ and —S—$R^5$—Z—$R^4$;

Z is oxygen or sulphur;

$R^5$ is selected from the group consisting of $C_{1-15}$-alkyl, $C_{2-15}$-alkenyl, and $C_{2-15}$-alkynyl;

Y is a 5 or 6 membered heterocyclic group; and

G is selected from one of the following azacyclic or azabicyclic ring systems:

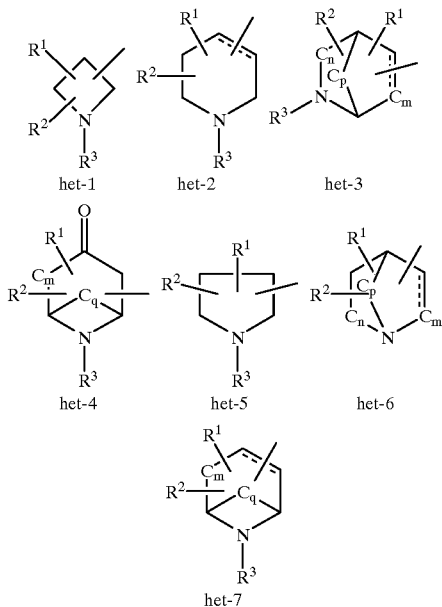

or

G can optionally be substituted $C_3$–$C_8$ cycloalkyl wherein the substitution is —$NR^6R^7$;

$R^6$ and $R^7$ independently are selected from the group consisting of hydrogen and $C_{1-6}$-alkyl; or $R^6$ and $R^7$ together with the nitrogen atom optionally form a 4- to 6-member ring;

$R^1$ and $R^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with a subsituent independently selected from the group consisting of —OH, —$COR^6$, $CH_2$—OH, halogen, —$NH_2$, carboxy, and phenyl;

$R^3$ is selected from the group consisting of hydrogen, $C_{1-5}$-alkyl, $C_{2-5}$-alkenyl and $C_{2-5}$-alkynyl;

$R^{6'}$ is selected from the group consisting of hydrogen and $C_{1-6}$-alkyl;

n is 0, 1 or 2;

m is 0, 1 or 2;

p is 0, 1 or 2;

q is 1 or 2;

r is 0, 1 or 2;

. . . is a single or double bond;

provided that when W is O and G is a saturated azabicyclic group having from 7 to 11 ring carbon atoms and a nitrogen atom wherein the nitrogen atom is separated from the W atom by 2 to 3 ring carbon atoms;

or a pharmaceutically acceptable salt or solvate thereof.

T) The G substituent is selected from the group consisting of

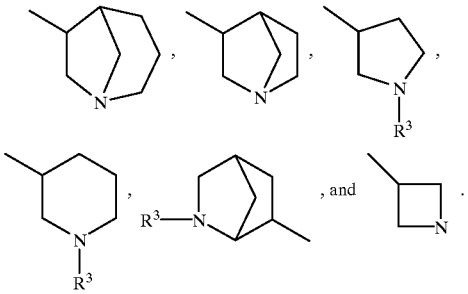

U) The G substituent is

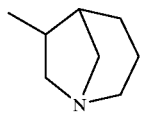

V) R is selected from the group consisting of —$SR^{4'}$, $SOR^{4'}$, —$SO_2R^{4'}$, substituted benzyloxycarbonyl wherein the substituents are one or more independently selected from the group consisting of —CN, —$OCF_3$, —$CF_3$, —$CONH_2$ and —$CSNH_2$; or $C_{3-10}$-cycloalkyl, $C_{4-12}$-(cycloalkylalkyl), —Z—$C_{3-10}$-cycloalkyl and —Z—$C_{4-12}$-(cycloalkylalkyl).

W) R is selected from the group consisting of $R^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl); and $R^4$ is selected from the group consisting of substituted $C_{5-15}$-alkyl, optionally substituted $C_{2-15}$-alkenyl, and optionally substituted $C_{2-15}$-alkynyl, wherein such substituent is one or more independently selected from the group consisting of halogen(s), —$CF_3$, —CN, Y, phenyl and phenoxy; wherein phenyl or phenoxy is optionally substituted with one or more substituents selected from the group consisting of halogen, —CN, $C_{1-4}$-alkyl, $C_{1-4}$-alkoxy, —$OCF_3$, —$CF_3$, —$CONH_2$ and —$CSNH_2$.

X) G is selected from the group consisting of het-4, het-7, het-6 wherein n=2; het-3 wherein one of n and m is 0 or 2; and het-3 wherein the l or l' group is attached at the bridgehead of het-3.

Especially preferred compounds of this invention have the characteristics of A-F,P; A-F,Q; characteristics of A, G, H, M, F; characteristics of G-O,Q; or the characteristics of G-J,M,P; or G-J,M,Q. The characteristics of R and S may be particularly preferred.

Further, especially preferred R groups include phenyl, benzyloxycarbonyl, —$OR^5Y$, —SR5Y, $OR^5$—Z—Y, —$SR^5ZY$, —O—$R^4$—Z—$R^5$ or —S—$R^4$—Z—$R^5$, —$SOR^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl) wherein Z is oxygen or sulphur, $R^5$ is $C_{1-15}$-alkyl, $C_{2-15}$-alkenyl, $C_{2-15}$-alkynyl, Y is a 5 or 6 membered heterocyclic group containing one to four N, O or S atom(s) or a combination thereof, $R_4$ is $C_{1-15}$-alkyl, $C_{2-15}$-alkenyl, and $C_{2-15}$-alkynyl.

Further, especially preferred G groups include the following heterocycles:

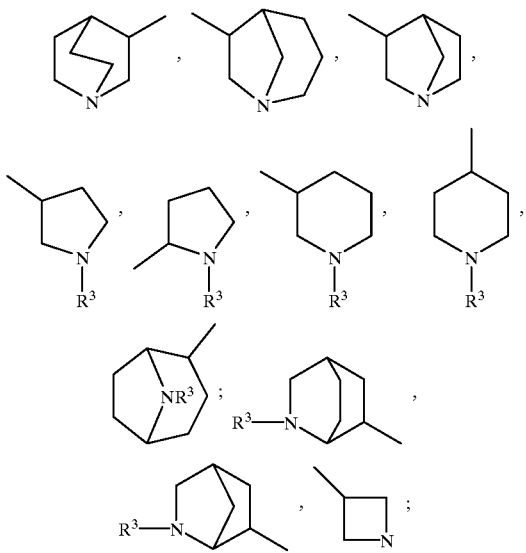

wherein the point of attachment to the —(CH$_2$)$_r$—W— group is as indicated

Some particularly preferred G groups include

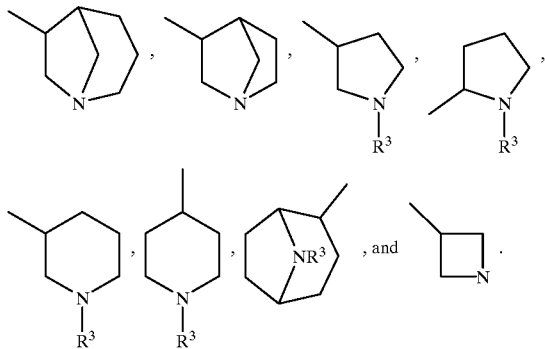

It is another preferred embodiment of this invention that G is not an azabicycle, particularly when w is oxygen.

Additionally, another embodiment of this invention which can be preferred is that when W is O and G is alkyl, R is not halogen.

The invention will now be described in further detail with reference to the following examples. The examples are provided for illustrative purposes, and are not to be construed as limiting the scope of the invention in any way.

EXAMPLE 1

(±)-3-Butyloxy-4-(1-azabicyclo[2.2.2]octyl-3-oxy) -1,2,5-oxadiazole

A suspension of 3,4-diphenylsulfonyl-1,2,5-oxadiazole oxide (4.6 g, 0.126 mol, Ref. *J.Chem. Soc.* 1964, 904.) in 1-butanol (400 mL) was heated to 55–60° C. as a solution of sodium 1-butyloxide (0.3 g Na, 40 mL 1-butanol) was added dropwise. After 1 h, the solvent was evaporated, residue was treated with H$_2$O, and the mixture extracted with ether (3×). The extracts were washed with H$_2$O, dried, and the solvent evaporated to give a white solid (3.15 g). The solid was heated to reflux overnight in P(OCH$_3$)$_3$ (30 mL) then poured into ice-H$_2$O containing HCl (6 mL, 5N). The mixture was extracted with ether, the extracts washed with brine, dried, and the solvent evaporated to give a yellow liquid. Radial chromatography (15% EtOAc/hexane) gave a clear liquid (1.85 g). The liquid was dissolved in THF (30 mL) and added dropwise to a mixture prepared from 1-azabicyclo[2.2.2]octan-3-ol(1.85 g 0.014 mol), THF (20 mL), and 1.6 M n-butyl lithium in hexane (8.4 mL, 0.013 mol). The reaction was then warmed to 52° C. for 5 h. The cooled reaction was acidified with dilute HCl and diluted wit ether. the aqueous fraction was washed with ether, made basic, and extracted with ether. The extracts were dried and evaporated to give a clear liquid. The HCl salt (1.4 g) crystallized from CHCl$_3$-EtOAc-ether, m.p. 186–188° C. (Compound 1).

EXAMPLE 2

(±)-3-Chloro-2-(1-azabicyclo[2.2.2]octyl-3-oxy)pyrazine

A solution of 1-azabicyclo[2.2.2]octan-3-ol (5 g, 0.039 mol) in THF (400 mL) was treated with 1.6 M n-butyllithium in hexane (25 mL, 0.04 mol). After 1 h, the solution was cooled in an ice-water bath and 2,3-dichloropyrazine (6.6 g, 0.044 mol) in THF (30 mol) was added in one portion. Cooling was removed and after 30 min., the reaction was heated to reflux for 2.5 h. The solvent was evaporated, the residue acidified with 1 N HCl, and the mixture extracted with ether. The aqueous fraction was made basic and extracted with ether. The extracts were washed with water, dried, and the solvent evaporated to give a tacky solid. Recrystallization from ether gave a yellow solid (1.74 g), m.p. 112.5–114° C. (Compound 2).

EXAMPLE 3

(±)-3-Butyloxy-2-(1-azabicyclo[2.2.2]octyl-3-oxy)pyrazine

A solution of sodium butyloxide (0.25 g Na, 0.0109 mol, 1-butanol, 30 mL) was added to (compound 2) (0.48 g, 0.002 mol), the reaction stirred overnight, then heated to 80° C. for 4 h. The solution was acidified and the solvent evaporated. The residue was suspended in H$_2$O, extracted with ether, and the aqueous solution made basic. The aqueous fraction was extracted with EtOAc, the extracts washed with H$_2$O, dried, and the solvent evaporated to give a yellow oil. The HCl salt (0.32 g) crystallized from EtoAc as a white powder, m.p. 150–151° C. (Compound 3).

EXAMPLE 4

(±)-3-Propyloxy-2-(1-azabicyclo[2.2.2]octyl-3-oxy) pyrazine

To a solution of lithium 1-propyloxide (7 mL 1.6 M n-butyllithium, 0.011 mol, 1-propanol, 30 mL) was added (compound 2) (0.63 g, 0.0026 mol) and the reaction heated to reflux for 6 h. The solvent was evaporated, the residue suspended in H$_2$O, and the mixture extracted with EtOAc. The extracts were washed with H$_2$O, dried, and the solvent evaporated to give an oil. The HCl salt (0.34 g) crystallized from acetone as a tan solid, m.p. 186–190° C. (Compound 4).

EXAMPLE 5

(±)-3-Hexyloxy-2-(1-azabicyclo[2.2.2]octyl-3-oxy) pyrazine

To a solution of lithium 1-hexyloxide (7.8 mL 1.6 M n-butyllithium, 0.013 mol. 1-hexanol, 20 mL) was added (compound 2) (0.6 g, 0.0025 mol) and the reaction heated to 80° C. overnight. The solution was cooled, treated with 1 N HCl (15 mL) and the solvent evaporated. The residue was suspended in H$_2$O, the mixture washed with ether, and made basic. The aqueous fraction was extracted with EtOAc, the

EXAMPLE 6

(±)-3-Butylthio-2-(1-azabicyclo[2.2.2]octyl-3-oxy)pyrazine

A solution of 1-butanethiol (1.1 mL) in THF (100 mL) was treated with 1.6 M n-butyl lithium in hexane (4.7 mL, 0.0075 mol). After 10 min, (compound 2) (0.6 g, 0.0025 mol) was added and the reaction heated to reflux for 3 h. The solvent was evaporated, the residue acidified with cold dilute HCl, and the mixture extracted with ether. The aqueous was made basic and extracted with ether. The ether was dried and the solvent evaporated to give a clear liquid. The HCl salt (0.59 g) crystallized from EtOAc as white crystals, m.p. 192–193° C. (Compound 6).

EXAMPLE 7

(±)-3-Pentylthio-2-(1-azabicyclo[2.2.2]octyl-3-oxy)pyrazine

A solution of 1-pentanethiol (1.2 mL) in THF (50 mL) was treated with 1.6 M n-butyl lithium in hexane (4.7 mL, 0.0075 mol). After 10 min, (compound 2) (0.6 g, 0.0025 mol) was added and the reaction heated to reflux for 2 h. The solvent was evaporated, the residue acidified with cold dilute HCl, and the mixture extracted with ether. The aqueous was made basic and extracted with ether. The aqueous was made basic and extracted with EtOAc. The EtOAc was dried and the solvent evaporated to give a clear liquid. The HCl salt (0.44 g) crystallized from EtOAc, m.p. 169–171° C. (Compound 7).

EXAMPLE 8

(±)-2-(1-Azabicyclo(2.2.2]octyl-3-oxy)pyrazine

A suspension of 60% NaH in oil (1 g, 0.025 mol) in DMF (30 mL) was treated with 1-azabicyclo[2.2.2]octan-3-ol (3.28 g, 0.025 mol) and the mixture heated to 50° C. for 65 min. The mixture was treated dropwise with 2-chloropyrazine (3.16 g, 0.027 mol) and heating continued for 3 h. Heating was discontinued and the reaction stirred overnight. The solvent was evaporated, the residue treated with water, acidified, and extracted with ether. The extracts were dried, the solvent evaporated, and the residue purified by radial chromatography (30% MeOH-EtOAc-trace N-H$_4$OH) to give an oil. The HCl salt (2.07 g) crystallized from MeOH-EtOAc, m.p. 256–258° C. (Compound 8).

EXAMPLE 9

(±)-3-(1-Pentyloxy)-2-(1-azabicyclo[2.2.2]octyl-3-oxy)pyrazine

To a solution of lithium 1-pentoxide (1.6 M n-butyllithium, 7.6 mL, 0.012 mol, 1-pentanol, 20 mL) was added (Compound 2) (0.58 g, 0.0024 mol) and the reaction heated to 90° C. overnight. The solution was acidified and the solvent evaporated. The residue was suspended in H$_2$O, extracted with ether, and the aqueous solution made basic. the aqueous fraction was extracted with EtOAc, the extracts washed with H$_2$O, dried, and the solvent evaporated to give an oil. The oil was purified by raidal chromatography (10% EtOH-1% N-H$_4$OH-CHCl$_3$) and the HCl salt (0.2 g) crystallized from EtOAc as a white powder, m.p. 163–165° C. (Compound 9).

EXAMPLE 10

(±)-3-Methoxy-2-(1-azabicyclo[2.2.2]octyl-3-oxy)pyrazine

To a solution of sodium methoxide (Na, 0.4 g, 0.0174 mol, methanol, 25 mL) was added (compound 2) 10.8 g, 0.0033 mol) and the reaction heated to reflux overnight. The solvent was evaporated, the residue suspended in H$_2$O, and the mixture extracted with EtOAc. The extracts were dried, the solvent evaporated, and the residue purified by radial chromatography (10% EtOH-1% NH$_4$OH-CHCl$_3$). The HCl salt (0.34 g) crystallized from 2-propanol as a hemihydrate, m.p. 215–218° C. (Compound 10).

EXAMPLE 11

(±)-3-Ethoxy-2-(1-azabicyclo[2.2.2]octyl-3-oxy)pyrazine

To a solution of sodium ethoxide (Na, 0.4 g, 0.0174 mol, ethanol, 25 mL) was added (compound 2) (0.8 g, 0.0033 mol) and the reaction heated to reflux overnight. The solvent was evaporated, the residue suspended in H$_2$O, and the mixture extracted with EtOAc. The extracts were dried, the solvent evaporated, and the residue purified by radial chromatography (10% EtOH-1% NH$_4$OH-CHCl$_3$). The HCl salt (0.086 g) crystallized from 2-propanol, m.p. 215–218° C. (Compound 11).

EXAMPLE 12

(±)-3-(1-Hexylthio)-2-(1-azabicyclo[2.2.2]octyl-3-oxy)pyrazine

A solution of 1-hexanethiol (1.4 mL) in THF (50 mL) was treated with 1.6 M n-butyllithium in hexane (4.7 mL, 0.0075 mol). After 10 min, (compound 2) (0.6 g, 0.0025 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried and the solvent evaporated to give a clear liquid. The HCl salt (0.57 g) crystallized from EtOAc, m.p. 171–174° C. (Compound 12).

EXAMPLE 13

(±)-3-Methylthio-2-(1-azabicyclo[2.2.2]octyl-3-oxy)pyrazine

A suspension of NaH (0.42 g, 0.018 mol) in DMF (25 mL) was treated with 5.19 M methanethiol in DMF (6.44 mL, 0.033 mol). After 10 min, (compound 2) (0.8 g, 0.0033 mol) was added and the reaction heated to 50° C. for 3 h. The reaction was cooled, acidified, and the solvent evaporated. The residue was suspended in cold water, extracted with ether, the aqueous made basic, and the mixture extracted with EtOAc. The EtOAc was dried and the solvent evaporated to give a clear liquid. The HCl salt (0.63 g) crystallized from MeOH-EtOAC, m.p. 243–247° C. (Compound 13).

EXAMPLE 14

(±)-3-Ethylthio-2-(1-azabicyclo[2.2.2]octyl-3-oxy)pyrazine

A solution of ethanethiol (2.6 mL) in THF (90 mL) was treated with 1.6 M n-butyllithium in hexane (9 mL, 0.0167 mol). After 15 min, (compound 2) (0.6 g, 0.0025 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried, the solvent evaporated, and the residue purified by radial chromatography (5% EtOH-0.5% NH$_4$OHCHCl$_3$). The HCl salt (0.48 g) crystallized from EtOAc, m.p. 269–272° C. (Compound 14).

EXAMPLE 15

(±)-3-(1-Propylthio-2-(1-azabicyclo[2.2.2]octyl-3-oxy) pyrazine

A solution of 1-propanethiol (2.7 mL) in THF (90 mL) was treated with 1.6 M n-butyllithium in hexane (7 mL, 0.0117 mol). After 15 min, (compound 2) (0.7 g, 0.0029 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried, the solvent evaporated to give an oil. The HCl salt (0.76 g) crystallized from MeOH-EtOAc, m.p. 231–234° C. (Compound 15).

EXAMPLE 16

(±)-3-(1-Heptylthio-2-(1-azabicyclo[2.2.2]octyl-3-oxy) pyrazine

A solution of 1-heptanethiol (4.9 mL) in THF (90 mL) was treated with 1.6 M n-butyllithium in hexane (7 mL, 0.0117 mol). After 15 min, (compound 2) (0.7 g, 0.0029 mol) was added and the reaction heated to reflux for 4 h. The solvent was evaporated, the residue acidified with cold dilute HCl, and the mixture extracted with ether. The aqueous was made basic and extracted with EtOAc. The EtOAc was dried, the solvent evaporated to give an oil. The HCl salt (0.767 g) crystallized from MeOH-EtOAc as a hemihydrate, m.p. 169–173° C. (Compound 16).

EXAMPLE 17

3-(1-Butylthio-2-(2-(dimethylamino)ethoxy)pyrazine

A solution of 2-dimethylaminoethanol (2.13 mL, 0.021 mol) in THF (130 mL) was treated with 1.6 M n-butyllithium in hexane (13.1 mL, 0.021 mol) with cooling in an ice-water bath. To the solution was added 2,3-dichloropyrazine (3.13 g, 0.021 mol) and the reaction heated to reflux overnight. The solvent was evaporated, the residue acidified with cold 1 N HCl, and the mixture extracted with ether. The aqueous was made basic and extracted with EtOAc. The extracts were washed with water, dried, and the solvent evaporated to give a clear oil (3.86 g). The oil was added to a solution of lithium 1-butanethioxide (1.6 M n-butanethioxide (1.6 M n-butyllithium, 17 mL, 0.0273 mol, 1-butanethiol, 19.7 mL, 0.184 mol) in THF (100 mL), the reaction heated to reflux for 2 h, heating removed, and the reaction stirred over the weekend. The solvent was evaporated, the residue dissolved in dilute HCl, and the mixture extracted with ether. The aqueous phase was made basic, extracted with EtOAc, the extracts dried, and the solvent evaporated. The residue was purified by radial chromatography (5% EtOH-0.5% NH$_4$OH-CHCl$_3$) to give an oil (3.4 g). The HCl salt crystallized from EtOAc to give a white solid, m.p. 120–123° C. (Compound 17).

EXAMPLE 18

3-(1-Butylthio)-2-(2-(trimethylamino)ethoxy)pyrazine iodide

A solution of (compound 17) (0.7 g, 0.0028 mol) in EtOAc (40 mL) was treated with iodomethane (0.4 mL) and the reaction stirred overnight. The white solid (1.04 g) was collected by filtration and dried, m.p. 140–142° C. (Compound 18).

EXAMPLE 19

3-Chloro-2-[endo-(+,−)-6-(1-azabicyclo[3.2.1]octyloxy)] pyrazine

A solution of potassium t-butoxide (0.62 g, 0.0055 mol) in THF (10 mL) was treated with endo-(+,−)-1-azabicyclo [3.2.1]octan-6-ol (0.64 g, 0.005 mol). After 5 min, 2,3-dichloropyrazine (2 g, 0.0134 mol) was added and the reaction stirred overnight. The reaction was diluted with H$_2$O, acidified, and extracted with ether. The aqueous phase was made basic and extracted with EtOAc, the extracts dried, washed with brine, dried, and the solvent evaporated. The residue was purified by radial chromatography (20% EtOH-2% NH$_4$OH-CHCl$_3$) to give an oil. The HCl salt crystallized from acetone (0.44 g), m.p. 200° C. dec. (Compound 19).

EXAMPLE 20

3-Methyl-2-[endo-(+,−)-6-(1-azabicyclo[3.2.1]octyloxy)] pyrazine

A solution of potassium t-butoxide (0.62 g, 0.0055 mol) in THF (10 mL) was treated with endo-(+,−)-1-azabicyclo [3.2.1]octan-6-ol (0.64 g, 0.005 mol). After 5 min, reaction was cooled in an ice-water bath and 2-chloro-3-methylpyrazine (1.3 g, 0.01 mol) was added in a single portion. Cooling was removed and the reaction stirred for 3 days. The solvent was evaporated, the residue diluted with H$_2$O, acidified, and extracted with ether. The aqueous phase was made basic and extracted with EtOAc, the extracts dried, washed with brine, dried, and the solvent evaporated. The residue was converted to an HCl salt and recrystallized from 2-propanol to give a floculant powder (0.5 g), m.p. 240° C. dec. (Compound 20).

EXAMPLE 21

2-[endo-(+,−)-6-(1-azabicyclo[3.2.1]octyloxy)]-pyrazine

A solution of potassium t-butoxide (0.62 g, 0.0055 mol) in THF (10 mL) was treated with endo-(+,−)-1-azabicyclo [3.2.1]octan-6-ol (0.64 g, 0.005 mol). After 5 min, reaction was cooled in an ice-water bath and 2-chloro-3-methylpyrazine (1.2 g, 0.01 mol) was added in a single portion. Cooling was removed and the reaction stirred 4 h. The solvent was evaporated, the residue diluted with H$_2$O, acidified, and extracted with ether. The aqueous phase was made basic and extracted with EtOAc, the extracts dried, washed with brine, dried, and the solvent evaporated. The solid residue was converted to an HCl salt and recrystallized from 2-propanol to give a white solid (0.92 g), m.p. 250° C. dec. (Compound 21).

EXAMPLE 22

6-Chloro-2-[endo-(+,−)-6-(1-azabicyclo[3.2.1]octyloxy)] pyrazine

A solution of potassium t-butoxide (0.62 g, 0.0055 mol) in THF (10 mL) was treated with endo-(+,−)-1-azabicyclo [3.2.1]octan-6-ol (0.64 g, 0.005 mol). After 5 min, reaction was cooled in an ice-water bath and 2,6-dichloropyrazine (1 g, 0.0067 mol) was added in a single portion. Cooling was removed and the reaction stirred over night. The solvent was evaporated, the residue diluted with H$_2$O, acidified, and extracted with ether. The aqueous phase was made basic and extracted with EtOAc, the extracts dried, washed with brine, dried, and the solvent evaporated. The residue was purified by radial chromatography (20% EtOH-2% NH$_4$OH-CHCl$_3$). The HCl salt crystallized from acetone to give a white solid (0.33 g), m.p. 211–213° C. dec. (Compound 22).

EXAMPLE 23

3-(1-butyloxy)-2-[endo-(+,−)-6-(1-azabicyclo[3.2.1] octyloxy)]-pyrazine

A solution of potassium t-butoxide (1 g, 0.0089 mol) in THF (20 mL) was treated with 1-butanol (1 mL). After 5 min, reaction was cooled in an ice-water bath and Compound 19 (0.65 g, 0.0027 mol) in THF (10 mL) was added. Cooling was removed and the reaction stirred for 3 days. The solvent was evaporated, the residue diluted with $H_2O$, acidified, and extracted with ether. The aqueous phase was made basic and extracted with EtOAc, the extracts dried, washed with brine, dried, and the solvent evaporated. The residue was purified by radial chromatography (20% EtOH-2% $NH_4OH$-$CHCl_3$). The HCl salt crystallized from EtOAc to give a white solid (0.23 g), m.p. 171.5–172.5° C. dec. (Compound 23)

EXAMPLE 24

3-(1-butylthio)-2-[endo-(+,−)-6-(1-azabicyclo[3.2.1] octyloxy)]-pyrazine

A solution of potassium t-butoxide (1 g, 0.0089 mol) in THF (20 mL) was cooled in ice-water and treated with 1-butanethiol (1 mL). After 5 min, cooling was removed and Compound 19 (0.6 g, 0.0025 mol) in THF (10 mL) was added. After stirring overnight, the solvent was evaporated, the residue diluted with $H_2O$, acidified, and extracted with ether. The aqueous phase was made basic and extracted with EtOAc, the extracts dried, washed with brine, dried, and the solvent evaporated. The residue was purified by radial chromatography (20% EtOH-2% $NH_4OH$-$CHCl_3$). The HCl salt crystallized from EtOAc to give a white solid (0.64 g), m.p. 157–158° C. dec. (Compound 24).

EXAMPLE 25 endo-(8-Methyl-8-azabicyclo[3.2.1]octyl-3-oxy)pyrazine

A solution of potassium tert-butoxide (0.62 g) in THF (15 mL) was treated with tropine (0.7 g). After 5 min, the reaction was cooled in ice-water and chloropyrazine (1.2 g) was added. The cooling was removed and the reaction stirred over night. The solvent was evaporated, the residue dissolved in cold 1 N HCl, and the mixture exracted with ether. The aqueous fraction was made basic, extracted with EtOAc, the extracts washed with water, brine, the solvent dried, and the solvent evaporated. The residue was purified by radial chromatography eluting with 20%-EtOH-2%-$NH_4OH$-$CHCl_3$ to give endo-(8-methyl-8-azabicyclo[3.2.1] octyl-3-oxy)pyrazine (0.6 g) that was isolated as a HCl salt that crystallized from 2-propanol, m.p. 240° C., dec. (Compound 25).

EXAMPLE 26

2-(2-Dimethylaminoethoxy)pyrazine

A solution of 2-dimethylaminoethanol (1 mL) in THF (20 mL) was treated with potassium tert-butoxide (1.2 g). After 5 min, chloropyrazine (2 g) was added and the reaction stirred 2 h. The solvent was evaporated, the residue suspended in cold water, the mixture acidified, and the mixture extracted with ether. The aqueous fraction was made basic and extracted with EtOAc. The extracts were dried, the solvent evaporated, and the residue purified by radial chromatography eluting with 10%-EtOH-1%-$NH_4OH$-$CHCl_3$ to give 2-(2-dimethylaminoethoxy)pyrazine (1.3 g). The HCl salt crystallized from 2-propanol as a white solid, m.p. 151–153° C. (Compound 26).

EXAMPLE 27

2-(2-Trimethylaminoethoxy)pyrazine iodide

A solution of the free base of Compound 26 (0.7 g) in EtOAc (40 mL) was treated with methyl iodide (1 mL) and the reaction stirred over night. The resulting solid was collected and dried to give 2-(2-trimethylaminoethoxy) pyrazine iodide as a off white solid (1.34 g), m.p. 164° C., dec. (Compound 27).

EXAMPLE 28

(S)-2-(1-Methyl-2-pyrrolidinylmethoxy)pyrazine

A solution of (S)-1-methyl-2-pyrrolidinemethanol (1.15 g) in THF (45 mL) was treated with potassium tert-butoxide (1.2 g). After 10 min, chloropyrazine was added and the reaction stirred for 1.5 h. The reaction was quenched with 5 N HCl (4 mL) and the solvent evaporated. The residue was suspended in water and extracted with ether. The aqueous fraction was made basic and extracted with $CHCl_3$. The extracts were dried, the solvent evaporated, and the residue purified by radial chromatography eluting with 20%-EtOH-2%-$NH_4OH$-$CHCl_3$ to give (S)-2-(1-methyl-2-pyrrolidinylmethoxy)pyrazine (1.1). The HCl salt crystallized from EtOAc as a white solid, m.p. 121–122° C. (Compound 28)

EXAMPLE 29

(±) -endo-2-Propylthio-3-(1-azabicyclo[3.2.1]octyl-6-oxy) pyrazine

Potassium t-butoxide (0.9 g, 8 mmoles) was added at 0° C. to propanethiol (0.61 g, 8 mmoles) in 20 ml THF and stirred for 5 min. Compound 19 (0.5 g, 2 mmoles) was added and the reaction stirred for 24 hr at room temperature. 200 ml of 1 N HCl was added and the aqueous solution washed with ethyl acetate. The pH was adjusted to 12.0. The product was extracted with ethyl acetate, dried over sodium sulfate and evaporated. The HCl salt was formed in ether and filtered to yield (±)-endo-2-propylthio-3-(1-azabicyclo [3.2.1]octyl-6-oxy)pyrazine hydrochloride (0.38 g), m.p. 159–160° C. (Compound 29)

The following compounds were prepared in substantially the same manner as Compound 29 by substituting the appropriate alkylthiol for propanethiol.

EXAMPLE 30

(±) -endo-2-Pentylthio-3-(1-azabicyclo[3.2.1]octyl-6-oxy) pyrazine

Obtained from Compound 19 and pentanethiol in 60% yield, m.p. 159–160° C. (Compound 30).

EXAMPLE 31

(±) -endo-2- (2-Methylpropylthio)-3-(1-azabicyclo[3.2.1] octyl-6-oxy)pyrazine

Obtained from Compound 19 and 2-methylpropanethiol in 8% yield, m.p. 142–143° C. (Compound 31).

EXAMPLE 32

(±)-endo-2-Ethylthio-3-(1-azabicyclo[3.2.1]octyl-6-oxy) pyrazine

Obtained from Compound 19 and ethanethiol in 53% yield, m.p. 196–197° C. (Compound 32).

EXAMPLE 33

(±)-endo-2-(2,2,2-Trifluoroethylthio)-3-(1-azabicyclo [3.2.1]octyl-6-oxy)pyrazine Obtained from Compound 19 and 2,2,2-trifluoroethanethiol in 14% yield, m.p. 116–117° C. (Compound 33).

EXAMPLE 34

(±)-endo-2-(trans-2-Butenylthio)-3-(1-azabicyclo[3.2.1]octyl-6-oxy)pyrazine

Obtained from Compound 19 and trans-2-butenethiol in 13% yield, m.p. 128–130° C. (Compound 34).

EXAMPLE 35

(±) -endo-2-(4,4,4-Trifluorobutylthio)-3-(1-azabicyclo[3.2.1]octyl-6-oxy)pyrazine Obtained from Compound 19 and 4,4,4-trifluorobutanethiol in 30% yield, m.p. 173–174° C. (Compound 35).

EXAMPLE 36

(±) -endo-2-(2-proenylthio)-3-(1-azabicyclo[3.2.1]octyl-6-oxy)pyrazine

Obtained from Compound 19 and 2-propenethiol in 70% yield, m.p. 254–255° C. (Compound 36).

EXAMPLE 37

(±)-endo-2-(3-Methylbutylthio)-3-(1-azabicyclo[3.2.1]octyl-6-oxy)pyrazine

Obtained from Compound 19 and 3-methylbutanethiol in 26% yield, m.p. 174–176° C. (Compound 37).

EXAMPLE 38

(±) -endo-2-(4-Trifluoromethoxybenzylthio)-3-(1-azabicyclo[3.2.1]octyl-6-oxy)pyrazine Obtained from Compound 19 and 4-trifluoromethoxybenzylthiol in 57% yield, m.p. 175–176° C. (Compound 38).

EXAMPLE 39

(±)-endo-2-Propylthio-6-(1-azabicyclo[3.2.1]octyl-6-oxy)pyrazine

Obtained from Compound 22 and propanethiol in 11% yield as a foam. (Compound 39).

EXAMPLE 40

(±)-endo-2-(2.2.2-Trifluoroethylthio)-6-(1-azabicyclo[3.2.1]octyl-6-oxy)pyrazine Obtained from Compound 22 and 2,2,2-trifluoroethanethiol in 7% yield, m.p. 125–126° C. (Compound 40).

EXAMPLE 41

(±)-endo-2-(2-Methoxyethylthio)-3-(1-azabicyclo[3.2.1]octyl-6-oxy)pyrazine

Compound 19 (1.15 g, 4.7 mmoles) and sodium sulfide (Na$_2$S·9H$_2$O), 1.68 g, 7 mmoles) were heated in 30 ml DMF at 50° C. for 3.5 hr, cooled to 0° C. and 2-Bromoethylmethylether (1.3 g, 9 mmoles) added. The reaction was stirred at room temperature overnight and diluted with ethyl acetate and 100 ml of 5 N HCl. The aqueous layer was washed with ethyl acetate and the pH adjusted to 12.0. The product was extracted with ethyl acetate, dried over sodium sulfate, condensed and purified by HPLC eluted with 94%CHCl$_3$/5% ethanol/1% ammonium hydroxide. The HCl salt was formed in ether and filtered to give (±)-endo-2-(2-methoxyethylthio)-3-(1-azabicyclo[3.2.1]octyl-6-oxy)pyrazine hydrochloride (0.3 g), m.p. 165–166° C. (Compound 41).

The following compounds were prepared in substantially the same manner as Compound 41 substituting the appropriate alkylhalide for 2-bromoethylmethylether.

EXAMPLE 42

(±) -endo-2- (3-Phenyl-2-propenylthio)-(1-azabicyclo[3.2.1]octyl-6-oxy)pyrazine

Obtained from Compound 19 and cinnamyl bromide in 36% yield, m.p. 165–167° C. (Compound 42).

EXAMPLE 43

(±) -endo-2-(4-Methyl-3-pentenylthio)-3-(1-azabicyclo[3.2.1]octyl-6-oxy)pyrazine Obtained from Compound 19 and 1-bromo-4-methyl-3-pentene in 8% yield as a foam. (Compound 43).

EXAMPLE 44

Alternate Synthesis of Compound 19

A sample of (±)-(endo)-1-Azabicyclo[3.2.1]octan-6-ol (3.0 g, 23.6 mmoles, was added to a stirred solution of potassium t-butoxide (2.9 g, 26 mmoles) in 60 ml THF at room temperature. The reaction was cooled to 5° C. and 2,3-dichloropyrazine (7.03 g, 47 mmoles) in 15 ml THF was added. The solution was stirred at room temperature for 2 hrs, condensed, and diluted with water and ethyl acetate. The organic solution was dried and condensed. Purification by HPLC eluting with 94% CHCl$_3$, 5% ethanol, 1% ammonium hydroxide yielded 4.9 g, (Compound 19).

We claim:

1. A compound of the formula:

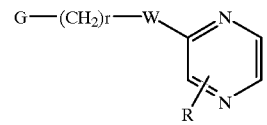

wherein

W is oxygen;

R is selected from the group consisting of hydrogen, amino, halogen, NHR$^6$, NR$^6$R$^7$, R$^4$, —OR$^4$, —SR$^4$, —SOR$^4$, —SO$_2$R$^4$, —Z—C$_{3-10}$-cycloalkyl, —Z—C$_{4-12}$-(cycloalkylalkyl), —O—R$^5$—Z—R$^4$ or —S—R$^5$—Z—R$^4$;

R$^4$ is selected from the group consisting of C$_{1-15}$-alkyl, C$_{2-15}$-alkenyl, or C$_{2-15}$-alkynyl, each of which is optionally substituted with one or more independently selected from the group consisting of halogen(s), —CF$_3$, —CN, phenyl and phenoxy wherein phenyl or phenoxy is optionally substituted with one or more selected from the group consisting of halogen, —CN, C$_{1-4}$-alkyl, C$_{1-4}$-alkoxy, —OCF$_3$, —CF$_3$, —CONH$_2$ and —CSNH$_2$;

Z is oxygen or sulphur;

R$^5$ is selected from the group consisting of C$_{1-15}$-alkyl, C$_{2-15}$-alkenyl, and C$_{2-15}$-alkynyl;

Z is oxygen or sulphur;

G is the azacyclic or azabicyclic ring system:

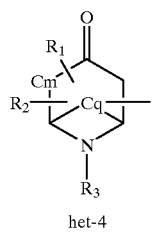

het-4

$R^1$ and $R^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with a substituent independently selected from the group consisting of —OH, —COR$^{6'}$, CH$_2$-OH, halogen, —NH$_2$, carboxy, and phenyl;

$R^{6'}$ is hydrogen or $C_{1-6}$-alkyl;

$R^3$ is selected from the group consisting of hydrogen, $C_{1-5}$-alkyl, $C_{2-5}$-alkyenyl, and $C_{2-5}$-alkynyl;

m and r, independently, are 0, 1 or 2;

q is 1 or 2;

or a pharmaceutically acceptable salt thereof.

2. A compound of claim 1 wherein R is —OR$^4$.

3. A compound of claim 2 wherein R$^4$ is $C_{1-15}$-alkyl.

4. A compound of claim 1 wherein R is —SR$^4$.

5. A compound of claim 4 wherein R$^4$ is $C_{1-15}$-alkyl.

6. A pharmaceutical formulation comprising a compound of claim 1 together with a pharmaceutically acceptable carrier or diluent.

7. A compound of the formula:

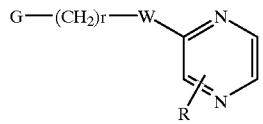

wherein

W is sulphur;

R is selected from the group consisting of hydrogen, amino, halogen, NHR$^6$, NR$^6$R$^7$, R$^4$, —OR$^4$, —SR$^4$, —SOR$^4$, —SO$_2$R$^4$, —Z—C$_{3-10}$-cycloalkyl, —Z—C$_{4-12}$-(cycloalkylalkyl), —O—R$^5$—Z—R$^4$ or —S—R$^5$-Z—R$^4$;

R$^4$ is selected from the group consisting of $C_{1-15}$-alkyl, $C_{2-15}$-alkenyl, or $C_{2-15}$-alkynyl, each of which is optionally substituted with one or more independently selected from the group consisting of halogen(s), —CF$_3$, —CN, phenyl and phenoxy wherein phenyl or phenoxy is optionally substituted with one or more selected from the group consisting of halogen, —CN, $C_{1-4}$-alkyl, $C_{1-4}$-alkoxy, —OCF$_3$, —CF$_3$, —CONH$_2$ and —CSNH$_2$;

Z is oxygen or sulphur;

R$^5$ is selected from the group consisting of $C_{1-15}$-alkyl, $C_{2-15}$-alkenyl, and $C_{2-15}$-alkynyl;

Z is oxygen or sulphur;

G is selected from one of the following the azacyclic or azabicyclic ring systems:

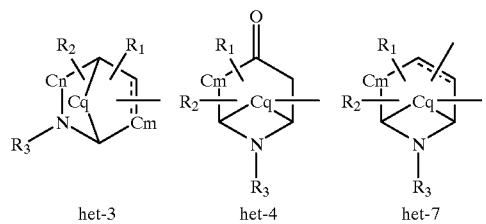

het-3　　het-4　　het-7

R$^1$ and R$^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with a substituent independently selected from the group consisting of —OH, —COR$^{6'}$, CH$_2$-OH, halogen, —NH$_2$, carboxy, and phenyl;

R$^{6'}$ is hydrogen or $C_{1-6}$-alkyl;

R$^3$ is selected from the group consisting of hydrogen, $C_{1-5}$-alkyl, $C_{2-5}$-alkyenyl, and $C_{2-5}$-alkynyl;

m, n, and r, independently, are 0, 1 or 2;

q is 1 or 2;

. . . is a single or double bond;

or a pharmaceutically acceptable salt thereof.

8. A compound of claim 7 wherein R is —OR$^4$.

9. A compound of claim 8 wherein R$^4$ is $C_{1-15}$-alkyl.

10. A compound of claim 7 wherein R is —SR$^4$.

11. A compound of claim 10 wherein R$^4$ is $C_{1-15}$-alkyl.

12. A compound of claim 7 wherein G is selected from the group consisting of

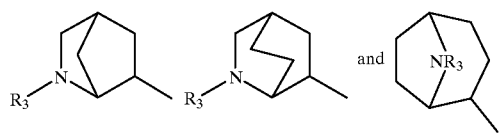

wherein R$_3$ is as defined in claim 7.

13. A pharmaceutical formulation comprising a compound of claim 1 together with a pharmaceutically acceptable carrier or diluent.

* * * * *

UNITED STATES PATENT AND TRADEMARK OFFICE
CERTIFICATE OF CORRECTION

PATENT NO. : 6,071,900

DATED : June 6, 2000

INVENTOR(S) : Leander Merritt and John S. Ward

It is certified that error appears in the above-indentified patent and that said Letters Patent is hereby corrected as shown below:

Column 30, lines 10 through 20 read:

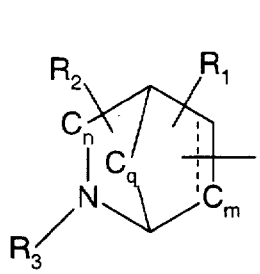 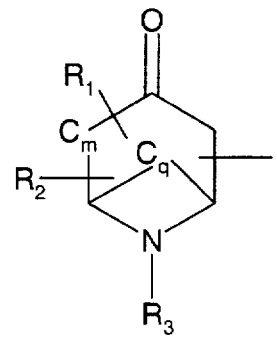 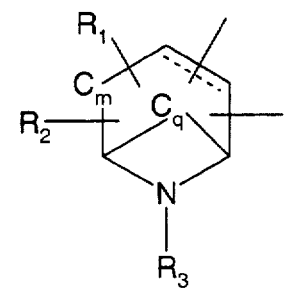

het-3                      het-4                    het-7

UNITED STATES PATENT AND TRADEMARK OFFICE
CERTIFICATE OF CORRECTION

PATENT NO. : 6,071,900
DATED : June 6, 2000
INVENTOR(S) : Leander Merritt and John S. Ward It is certified that error appears in the above-indentified patent and that said Letters Patent is hereby corrected as shown below:

And should read:

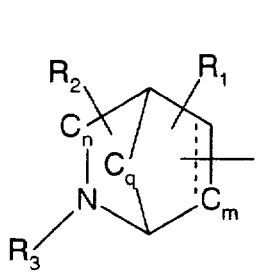
het-3

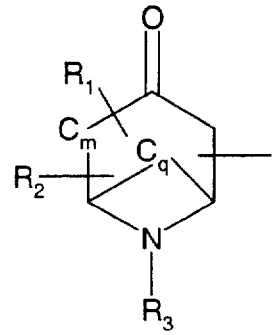
het-4

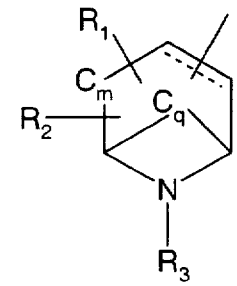
het-7

Signed and Sealed this

Seventeenth Day of April, 2001

*Attest:*

NICHOLAS P. GODICI

*Attesting Officer*   *Acting Director of the United States Patent and Trademark Office*